United States Patent [19]

Yamamoto

[11] 4,395,398
[45] Jul. 26, 1983

[54] DENTAL HEMOSTATIC COMPOSITION
[75] Inventor: Hiroji Yamamoto, Kawabe, Japan
[73] Assignee: Bee Brand Medico Dental Co., Ltd., Osaka, Japan
[21] Appl. No.: 249,726
[22] Filed: Mar. 31, 1981
[30] Foreign Application Priority Data

Apr. 2, 1980 [JP] Japan .................................. 55-43973

[51] Int. Cl.³ ...................... A61K 33/30; A61K 33/26; A61K 7/16; A61K 33/06
[52] U.S. Cl. ....................................... 424/145; 424/49; 424/56; 424/147; 424/154; 424/180
[58] Field of Search .................... 424/49, 56, 145, 147, 424/154

[56] References Cited

U.S. PATENT DOCUMENTS

| | | | |
|---|---|---|---|
| 2,492,085 | 12/1949 | Andersen | 424/154 |
| 2,890,987 | 6/1959 | Hilfer | 424/154 |
| 3,102,114 | 8/1963 | Komori et al. | 424/49 |
| 3,639,563 | 2/1972 | Januszewski | 424/49 |
| 3,641,238 | 2/1972 | Januszewski | 424/49 |
| 3,772,431 | 11/1973 | Mlkvy et al. | 424/49 |
| 3,888,976 | 6/1975 | Mlkvy et al. | 424/49 |
| 4,166,108 | 8/1979 | Brown et al. | 424/145 |
| 4,260,597 | 4/1981 | Porteous | 424/49 |

*Primary Examiner*—Douglas W. Robinson
*Attorney, Agent, or Firm*—Berman, Aisenberg & Platt

[57] ABSTRACT

A liquid hemostatic composition for local application to small hemorrhage in the dental field which comprises one or more astringents selected from the group consisting of aluminum chloride, tannic acid, ferric chloride, zinc chloride and potassium aluminum sulfate; one or more surfactants selected from the group consisting of cetyl pyridinium chloride, benzalkonium chloride, benzethonium chloride, chlorhexidine, chlorhexidine gluconate, lauryl sulfate, a polyoxyethylene sorbitan fatty acid ester, a polyoxyethylene fatty acid ester, a polyoxyethylene higher alcohol ether, a polyoxyethylene alkyl aryl ether, a polyoxyethylene lanolin derivative, a polyoxyethylene lanolin alcohol derivative, a polyoxyethylene castor oil derivative, a polyoxypropylene-polyoxyethylene alkyl ether and a polyoxyethylene alkylphenol-formaldehyde condensate; and a carrier or diluent selected from the group consisting of water and a mixture of water and one or more pharmaceutically acceptable water-soluble organic solvents.

8 Claims, No Drawings

DENTAL HEMOSTATIC COMPOSITION

The present invention relates to a dental hemostatic composition. More particularly, it relates to a hemostatic composition for local application to small hemorrhage in the dental field.

An aqueous solution or dispersion containing 10 to 40 w/v% of an astringent, such as tannic acid, aluminum chloride, zinc chloride or ferric chloride, has been used as a hemostatic composition for local application to small hemorrhages in the dental field, for example, bleeding from gums, which occurs during gingival preparation, gum displacement or scaling of the teeth in a dental hospital or other bleeding from mucosa in the mouth.

When this dental hemostatic composition is applied to a bleeding part, the astringent therein exerts its vasoconstriction and astriction activities and blood coagulation activity on superficial capillary vessels; the composition thereby manifests its hemostatic effect. However, in general, a certain length of time is required so that the composition manifests its hemostatic effect after application thereof to a bleeding part (hereinafter, this time being referred to as hemostasis time). On the other hand, it is desirable for the hemostasis time to be as short as possible so that treatment in a dental hospital is quickly and efficiently performed.

As a result of the present inventor's intensive study, it has been unexpectedly found that the hemostasis time is remarkably shortened by using an astringent together with a surfactant.

The main object of the present invention is to provide a dental hemostatic composition which can stop bleeding in a very short period of time in comparison with a conventional dental hemostatic composition. This object as well as other objects and advantages of the present invention will become apparent to those skilled in the art from the following description.

According to the present invention, there is provided a liquid dental hemostatic composition which comprises one or more astringents selected from the group consisting of aluminum chloride, tannic acid, ferric chloride, zinc chloride and potassium aluminum sulfate; one or more surfactants selected from the group consisting of cationic surfactants, anionic surfactants and nonionic surfactants; and a carrier or diluent selected from the group consisting of water and a mixture of water and one or more pharmaceutically-acceptable water-soluble organic solvents.

Since the surfactant is present in the dental hemostatic composition of the present invention, the length of time required to coagulate blood (hereinafter, this time being referred to as blood coagulation time) of the composition is less than one tenth as long as that of a conventional dental hemostatic composition which is a mere solution or dispersion of an astringent in water; a composition of the present invention thus quickly manifests its hemostatic effect, and the hemostasis time thereof is remarkably shortened.

In the present invention, the astringents selected from the group consisting of aluminum chloride, tannic acid, ferric chloride, zinc chloride and potassium aluminum sulfate can be used alone or in a combination thereof. The amount of astringent in the composition varies according to the particular compound selected, but, in general, it is desirable to use 5 to 30 w/v%, preferably 10 to 30 w/v%, of aluminum chloride, 10 to 35 w/v%, preferably 10 to 30 w/v%, of tannic acid, 5 to 25 w/v%, preferably 5 to 20 w/v%, of ferric chloride, 10 to 45 w/v%, preferably 10 to 40 w/v%, of zinc chloride and/or 1 to 10 w/v%, preferably 5 to 10 w/v%, of potassium aluminum sulfate, based on the total amount of the composition.

Examples of the surfactants used in the present invention are cationic surfactants, such as cetyl pyridinium chloride, benzalkonium chloride, benzethonium chloride, chlorhexidine and chlorhexidine gluconate; anionic surfactants, such as sodium lauryl sulfate; and nonionic surfactants, such as a polyoxyethylene sorbitan fatty acid ester, a polyoxyethylene fatty acid ester, a polyoxyethylene higher alcohol ether, a polyoxyethylene alkyl aryl ether, a polyoxyethylene lanolin derivative, a polyoxyethylene lanolin alcohol derivative, a polyoxyethylene castor oil derivative, a polyoxypropylene-polyoxyethylene alkyl ether and a polyoxyethylene alkylphenolformaldehyde condensate. The surfactants can be used alone or in any combination thereof and, in general, they are used in a concentration of 0.01 to 2.0 w/v%, preferably 0.05 to 1.0 w/v%, based on the total amount of the composition.

The dental hemostatic composition of the present invention is in the form of liquid prepared by dissolving or dispersing the astringent and the surfactant in a carrier or diluent, such as water or a mixture of water and one or more pharmaceutically-acceptable water-soluble organic solvents. Examples of the water-soluble organic solvents are ethanol, propylene glycol, glycerin, butanediol and a polyoxyethylene glycol (polymerization degree: 200–400) and they can be used alone or in any combination thereof. The ratio of the solvent to water is not critical.

The dental hemostatic composition of the present invention can be prepared according to a conventional method, such as mixing and dissolving or dispersing the appropriate ingredients. Optionally, the composition may be incorporated with other pharmacologically-active ingredients. For example, in order to relieve pain and stimulation at a bleeding part, a surface anesthetic, such as ethyl aminobenzoate, lidocaine or tetracaine, can be added to the composition.

The dental hemostatic composition of the present invention can be used by locally applying an appropriate amount thereof on a bleeding part of gums or mucosa in the mouth.

The following examples further illustrate the present invention in detail but are not to be construed to limit the scope thereof.

EXAMPLE 1

A mixture of aluminum chloride (25 g) and cetyl pyridinium chloride (0.5 g) was dissolved in water and the total volume thereof was adjusted to 100 ml with water to give the desired liquid dental hemostatic composition.

EXAMPLE 2

A mixture of aluminum chloride (25 g) and cetyl pyridinium chloride (0.1 g) was dissolved in water, and the total volume thereof was adjusted to 100 ml with water to give the desired liquid dental hemostatic composition.

EXAMPLE 3

A mixture of aluminum chloride (25 g) and cetyl pyridinium chloride (0.05 g) was dissolved in water and the total volume thereof was adjusted to 100 ml with water to give the desired liquid dental hemostatic composition.

EXAMPLE 4

A mixture of aluminum chloride (25 g) and benzalkonium chloride (0.5 g) was dissolved in water and the total volume thereof was adjusted to 100 ml with water to give the desired liquid dental hemostatic composition.

EXAMPLE 5

A mixture of aluminum chloride (25 g) and benzethonium chloride (0.5 g) was dissolved in water and the total volume thereof was adjusted to 100 ml with water to give the desired liquid dental hemostatic composition.

EXAMPLE 6

A mixture of aluminum chloride (25 g) and cetyl pyridinium chloride (0.5 g) was dissolved in aqueous 50% ethanol and the total volume thereof was adjusted to 100 ml with the same solvent to give the desired liquid dental hemostatic composition.

EXAMPLE 7

A mixture of aluminum chloride (25 g) and cetyl pyridinium chloride (0.5 g) was dissolved in aqueous 20% ethanol and the total volume thereof was adjusted to 100 ml with the same solvent to give the desired liquid dental hemostatic composition.

EXAMPLE 8

A mixture of ferric chloride (10 g) and cetyl pyridinium chloride (0.5 g) was dissolved in water and the total volume thereof was adjusted to 100 ml with water to give the desired dental hemostatic composition.

EXAMPLE 9

A mixture of zinc chloride (40 g) and cetyl pyridinium chloride (0.5 g) was dissolved in water and the total volume thereof was adjusted to 100 ml with water to give the desired dental hemostatic composition.

EXAMPLE 10

A mixture of tannic acid (30 g) and cetyl pyridinum chloride (0.5 g) was dissolved in water and the total volume thereof was adjusted to 100 ml with water to give the desired dental hemostatic composition.

EXAMPLE 11

A mixture of tannic acid (30 g) and sodium lauryl sulfate (0.5 g) was dissolved in water and the total volume thereof was adjusted to 100 ml with water to give the desired dental hemostatic composition.

EXAMPLE 12

A mixture of potassium aluminum sulfate (10 g) and cetyl pyridinium chloride (0.5 g) was dissolved in water and the total volume thereof was adjusted to 100 ml with water to give the desired dental hemostatic composition.

EXAMPLE 13

A mixture of aluminum chloride (25 g) and benzethonium chloride (0.5 g) was dissolved in aqueous 20% ethanol and the total volume thereof was adjusted to 100 ml with the same solvent to give the desired dental hemostatic composition.

EXAMPLE 14

A mixture of aluminum chloride (25 g) and polyoxyethylene sorbitan monopalmitate (0.5 g) was dissolved in water and the total volume thereof was adjusted to 100 ml with water to give the desired dental hemostatic composition.

EXAMPLE 15

A mixture of aluminum chloride (25 g), polyoxyethylene sorbitan monopalmitate (0.25 g) and cetyl pyridinium chloride (0.25 g) was dissolved in water and the total volume thereof was adjusted to 100 ml with water to give the desired dental hemostatic composition.

EXAMPLE 16

A mixture of aluminum chloride (25 g) and cetyl pyridinium chloride (0.5 g) was dissolved in aqueous 50% propylene glycol and the total volume thereof was adjusted to 100 ml with the same solvent to give the desired hemostatic composition.

EXAMPLE 17

A mixture of aluminum chloride (10 g) and cetyl pyridinium chloride (0.5 g) was dissolved in water and the total volume thereof was adjusted to 100 ml with water to give the desired composition.

EXAMPLE 18

A mixture of aluminum chloride (5 g) and cetyl pyridinium chloride (0.5 g) was dissolved in water and the total volume thereof was adjusted to 100 ml with water to give the desired composition.

EXAMPLE 19

A mixture of aluminum chloride (25 g) and sodium lauryl sulfate (0.5 g) was dissolved in water and the total volume thereof was adjusted to 100 ml with water to give the desired composition.

EXAMPLE 20

A mixture of aluminum chloride (10 g) and sodium lauryl sulfate (0.5 g) was dissolved in water and the total volume thereof was adjusted to 100 ml with water to give the desired composition.

EXAMPLE 21

A mixture of aluminum chloride (5 g) and sodium lauryl sulfate (0.5 g) was dissolved in water and the total volume thereof was adjusted to 100 ml with water to give the desired composition.

EXAMPLE 22

A mixture of tannic acid (20 g) and cetyl pyridinium chloride (0.5 g) was dissolved in water and the total volume thereof was adjusted to 100 ml with water to give the desired composition.

EXAMPLE 23

A mixture of tannic acid (10 g) and cetyl pyridinium chloride (0.5 g) was dissolved in water and the total volume thereof was adjusted to 100 ml with water to give the desired composition.

EXAMPLE 24

A mixture of tannic acid (5 g) and cetyl pyridinium chloride (0.5 g) was dissolved in water and the total volume thereof was adjusted to 100 ml with water to give the desired composition.

EXAMPLE 25

A mixture of tannic acid (20 g) and sodium lauryl sulfate (0.5 g) was dissolved in water and the total volume thereof was adjusted to 100 ml with water to give the desired composition.

EXAMPLE 26

A mixture of tannic acid (10 g) and sodium lauryl sulfate (0.5 g) was dissolved in water and the total volume thereof was adjusted to 100 ml with water to give the desired composition.

EXAMPLE 27

A mixture of tannic acid (5 g) and sodium lauryl sulfate (0.5 g) was dissolved in water and the total volume thereof was adjusted to 100 ml with water to give the desired composition.

EXAMPLE 28

A mixture of ferric chloride (25 g) and cetyl pyridinium chloride (0.5 g) was dissolved in water and the total volume thereof was adjusted to 100 ml with water to give the desired composition.

The following tests illustrate hemostatic effect of the dental hemostatic composition of the present invention.

(1) Blood coagulation test

Each composition of the above examples (0.5 ml) was added to whole blood of guinea pig (0.5 ml) to which heparin sodium (10 mg/ml) had been added and the blood coagulation time was recorded. As a control, the same procedure was repeated by using a conventional dental hemostatic composition which was a mere solution of an astringent in water. The results are shown in Table 1.

TABLE 1

| Ex. No. | Astringents Compound | w/v % | Surfactants Compound | w/v % | Blood coagulation time (sec.) |
|---|---|---|---|---|---|
| 1 | aluminum chloride | 25 | cetyl pyridinium chloride | 0.5 | 30–40 |
| 2 | aluminum chloride | 25 | cetyl pyridinium chloride | 0.1 | 90–100 |
| 3 | aluminum chloride | 25 | cetyl pyridinium chloride | 0.01 | 100 |
| 17 | aluminum chloride | 10 | cetyl pyridinium chloride | 0.5 | 30–40 |
| 18 | aluminum chloride | 5 | cetyl pyridinium chloride | 0.5 | 50–60 |
| 4 | aluminum chloride | 25 | benzalkonium chloride | 0.5 | 50–60 |
| 5 | aluminum chloride | 25 | benzethonium chloride | 0.5 | 50–60 |
| 19 | aluminum chloride | 25 | sodium lauryl sulfate | 0.5 | 30–40 |
| 20 | aluminum chloride | 10 | sodium lauryl sulfate | 0.5 | 40–50 |
| 21 | aluminum chloride | 5 | sodium lauryl sulfate | 0.5 | 50–60 |
| 10 | tannic acid | 30 | cetyl pyridinium chloride | 0.5 | 30–40 |
| 22 | tannic acid | 20 | cetyl pyridinium chloride | 0.5 | 30–40 |
| 23 | tannic acid | 10 | cetyl pyridinium chloride | 0.5 | 30–40 |
| 24 | tannic acid | 5 | cetyl pyridinium chloride | 0.5 | 50–60 |
| 11 | tannic acid | 30 | sodium lauryl sulfate | 0.5 | 30–40 |
| 25 | tannic acid | 20 | sodium lauryl sulfate | 0.5 | 30–40 |
| 26 | tannic acid | 10 | sodium lauryl sulfate | 0.5 | 30–40 |
| 27 | tannic acid | 5 | sodium lauryl sulfate | 0.5 | 50–60 |
| 28 | ferric chloride | 25 | cetyl pyridinium chloride | 0.5 | 30–50 |
| 12 | potassium aluminum sulfate | 10 | cetyl pyridinium chloride | 0.5 | 20–40 |
| Control | aluminum chloride | 25 | — | — | 900 |
| | tannic acid | 30 | — | — | * |
| | ferric chloride | 25 | — | — | 300 |
| | potassium aluminum sulfate | 10 | — | — | 1800 |

*The mixture became thick about 20 seconds after mixing the composition with whole blood but blood coagulation was not observed.

As is clear from the results shown in Table 1, since the surfactant is present in the composition of the present invention, the blood coagulation time thereof is remarkably shortened in comparison with that of the conventional composition used as the control.

(2) Hemostasis test

Gums of male Wistar rats (weight: 180-200 g, 3 rats per group) were laterally cut in a straight line with a surgical knife to bleed. The hemostatic composition of the present invention was applied on each bleeding part with a cotton swab and the hemostasis time was recorded. Hemostasis was confirmed by wiping the bleeding part with another swab and observing whether the swab was stained with blood or not. As a control, the same procedure was repeated by using a conventional hemostatic composition which was a 25 w/v% solution of aluminum chloride in water. The results are shown in Table 2.

TABLE 2

| Ex. No. | Astringents Compound | w/v % | Surfactants Compound | w/v % | Hemostasis time (sec.) |
|---|---|---|---|---|---|
| 1 | aluminum chloride | 25 | cetyl pyridinium chloride | 0.5 | $\leq 10$ |
| 2 | aluminum chloride | 25 | cetyl pyridinium chloride | 0.1 | $\leq 30$ |
| — | aluminum chloride | 25 | — | — | 1800–3600 |

As is clear from the results shown in Table 2, the hemostasis time of the composition of the present invention is remarkably shortened in comparison with that of the conventional composition.

(3) Clinical test

Hemostatic effect of the composition of Example 1 (containing 25 g of aluminum chloride and 0.5 g of cetyl pyridinium chloride per 100 ml of the composition) was clinically evaluated in gingival preparation, gum displacement or the treatment of gingival injured subjects by applying the composition on a bleeding part with a cotton swab. The blooding part was rinsed with water 1 minute after application of the composition and whether bleeding was stopped or not was observed. If bleeding was not stopped, the composition was again applied on the part and this procedure was repeated. Hemostatic effect was evaluated according to the following standard:

very good: bleeding was stopped by applying the composition once (1 minute).
good: bleeding was stopped by applying the composition twice (2 minutes).
average: bleeding was stopped by applying the composition three times (3 minutes).
inefficient: bleeding was not stopped.

The results are shown in Table 3.

TABLE 3

| Hemostatic effect | Gingival preparation case numbers | % | Gum displacement case numbers | % | Gingival injury case numbers | % |
|---|---|---|---|---|---|---|
| very good | 5 | 55.6 | 5 | 71.4 | 43 | 66.2 |
| good | 4 | 44.4 | 1 | 14.3 | 20 | 30.8 |
| average | 0 | 0.0 | 1 | 14.3 | 2 | 3.1 |
| inefficient | 0 | 0.0 | 0 | 0.0 | 0 | 0.0 |

The results in Table 3 are summarized in Table 4 together with those obtained by using 25 w/v% solution of aluminum chloride in water and 0.1 w/v% solution of epinephrine in water in the same procedure.

TABLE 4

| Hemostatic effect | Composition of Example 1 case numbers | % | 25% Aqueous solution of AlCl$_3$ case numbers | % | 0.1% Aqueous solution of epinephrine case numbers | % |
|---|---|---|---|---|---|---|
| very good | 53 | 65.4 | 4 | 18.2 | 8 | 34.8 |
| good | 25 | 30.9 | 6 | 27.3 | 9 | 39.1 |
| average | 3 | 3.7 | 10 | 45.5 | 5 | 21.7 |
| inefficient | 0 | 0.0 | 2 | 9.0 | 1 | 4.4 |

Statistical analysis of the data in Table 4 are shown in Table 5.

TABLE 5

| | Composition of Example 1 case numbers | % | 25% Aqueous solution of AlCl$_3$ case numbers | % | 0.1% Aqueous solution of epinephrine case numbers | % |
|---|---|---|---|---|---|---|
| very good + good | 78 | 96.3 | 10 | 45.5 | 17 | 73.9 |
| average + inefficient | 3 | 3.7 | 12 | 54.5 | 6 | 26.1 |
| $\chi^2$ - test | | | $\chi_0^2 = 31.97$ $p<0.001$ | | $\chi_0^2 = 8.69$ $p<0.01$ | |

As is clear from the results shown in Tables 4 and 5, the dental hemostatic composition of the present invention shows excellent hemostatic effect.

What is claimed is:

1. A liquid dental hemostatic composition consisting essentially of astringent, surfactant and carrier or diluent, said astringent being a member selected from the group consisting of aluminum chloride, tannic acid, ferric chloride, zinc chloride and potassium aluminum sulfate and the amount of aluminum chloride being from 5 to 30 w/v%, the amount of tannic acid being 10 to 35 w/v%, the amount of ferric chloride being 5 to 25 w/v%, the amount of zinc chloride being 10 to 45 w/v% and the amount of potassium aluminum sulfate being 1 to 10 w/v%, said surfactant being a member selected from the group consisting of cetyl pyridinium chloride, benzalkonium chloride, benzethonium chloride, sodium lauryl sulfate and a polyoxyethylene sorbitan fatty acid ester and the amount thereof being 0.01 to 2.0 w/v%, and said carrier or diluent being a member selected from the group consisting of water and a mixture of water with ethanol, propylene glycol, glycerin or a polyoxyethylene glycol having polymerization degree of 200 to 400, all percentages being based on the total composition.

2. A composition according to claim 1 wherein the astringent is aluminum chloride.

3. A composition according to claim 1 wherein the astringent is tannic acid.

4. A composition according to claim 1 wherein the astringent is ferric chloride.

5. A composition according to claim 1 wherein the astringent is zinc chloride.

6. A composition according to claim 1 wherein the astringent is potassium aluminum sulfate.

7. A method of improving hemostatic properties of an astringent-containing liquid dental composition, wherein the astringent comprises a member selected from the group consisting of aluminum chloride, tannic acid, ferric chloride, zinc chloride and potassium aluminum sulfate, which comprises incorporating in the composition from 0.01 to 2.0 w/v%, based on the total amount of said composition, of a surfactant selected from the group consisting of cetyl pyridinium chloride, benzalkonium chloride, benzethonium chloride, sodium lauryl sulfate and a polyoxyethylene sorbitan fatty acid ester.

8. A method of hemostasis of a small hemorrhage in the mouth which comprises locally applying, on a bleeding part of gums or mucosa in the mouth, an effective amount of a composition according to one of claims 2 to 6 and 1.

* * * * *